(12) United States Patent
Irving et al.

(10) Patent No.: US 6,506,774 B1
(45) Date of Patent: Jan. 14, 2003

(54) USE OF OREXIN RECEPTOR ANTAGONISTS

(75) Inventors: Elaine Alison Irving, Bengeo (GB); Gareth John Sanger, Sawbridgeworth (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/913,230

(22) PCT Filed: Feb. 10, 2000

(86) PCT No.: PCT/EP00/01147

§ 371 (c)(1),
(2), (4) Date: Nov. 30, 2001

(87) PCT Pub. No.: WO00/47284

PCT Pub. Date: Aug. 17, 2000

(30) Foreign Application Priority Data

| Feb. 12, 1999 | (GB) | 9903265 |
| Feb. 12, 1999 | (GB) | 9903278 |
| Feb. 12, 1999 | (GB) | 9903282 |
| Feb. 12, 1999 | (GB) | 9903284 |
| Mar. 17, 1999 | (GB) | 9906061 |

(51) Int. Cl.[7] .............................................. A61K 31/47
(52) U.S. Cl. ........................ 514/311; 514/312; 514/313
(58) Field of Search ................................. 514/311, 312, 514/313

(56) References Cited

FOREIGN PATENT DOCUMENTS

| EP | 0 849 361 A1 | 6/1998 | ............ C12N/15/12 |
| EP | 0 875 565 A2 | 11/1998 | ............ C12N/15/12 |
| EP | 0 875 566 A2 | 11/1998 | ............ C12N/15/12 |
| EP | 0 893 498 A2 | 1/1999 | ............ C12N/15/12 |
| WO | WO 96/34877 | 11/1996 | ............ C07H/21/04 |
| WO | WO 99/09024 | 2/1999 | ......... C07D/401/12 |
| WO | WO 99/30670 | 6/1999 | |
| WO | WO 99/58533 | 11/1999 | ......... C07D/471/04 |
| WO | WO 00/27845 | 5/2000 | ......... C07D/471/10 |

OTHER PUBLICATIONS

A. Kirchgessner and M. Liu, (Reprint) "Orexin Synthesis and Response in the Gut", *Neuron*, vol. 24, No. 4, pp. 941–951 (1999), Publisher: Cell Press.

*Primary Examiner*—Raymond Henley, III
(74) *Attorney, Agent, or Firm*—Kathryn L. Sieburth; Mary E. McCarthy; Charles M. Kinzig

(57) ABSTRACT

The use of orexin receptor antagonists as neuroprotectants, and in the treatment of nausea and vomiting, irritable bowel syndrome and other conditions associated with visceral pain.

10 Claims, No Drawings

USE OF OREXIN RECEPTOR ANTAGONISTS

This is a 371 of PCT/EP00/01147 filed Feb. 10, 2002.

The present invention relates to the use of orexin receptor antagonists as neuroprotectants, and in the treatment of nausea and vomiting, irritable bowel syndrome and other conditions associated with visceral pain.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in U.S. Pat. Nos. 5,935,814, 6,020,157 and 6,410,701. Polypeptides and polynucleotides encoding a second human orexin receptor, orexin-2 (HFGANP), have been identified and are disclosed in U.S. Pat. No. 6,166,193.

Polypeptides and polynucleotides encoding polypeptides which are ligands for the orexin-1 receptor, e.g. orexin-A (Lig72A) are disclosed in U.S. Pat. No. 6,309,854.

Orexin receptors are found in the mammalian host and may be responsible for many biological functions.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see *Cell,* 1998, 92, 573–585.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

Orexin-1 receptor mRNA and immunoreactivity is widely distributed throughout the brain including regions such as the hypothalamus, hippocampus and various other limbic and cortical areas. Thus the receptor is found in brain areas which have been reported to be affected by stroke in man and experimental stroke animals and head injury in man and experimental animals, to be involved in emesis and to be involved in visceral pain.

U.S. Pat. Nos. 6,410,529 and 6,372,757 disclose various phenyl urea derivatives as orexin receptor antagonists.

It has now been discovered that compounds possessing orexin receptor antagonist activity, in particular orexin-1 receptor antagonist activity, also demonstrate neuroprotectant properties. Therefore, such compounds are useful in the treatment and/or prophylaxis of disorders associated with neuronal degeneration resulting from ischaemic events in mammals, such as humans, including cerebral ischaemia after cardiac arrest, stroke and multi-infarct dementia, cerebral ischaemic events such as those resulting from surgery and/or during childbirth, and disorders resulting from traumatic head injury and subsequent haemorrhaging.

In particular the compounds are useful in the treatment and/or prophylaxis of stroke (ischaemic or haemorrhagic) or sub-arachnoid haemorrhage e.g. sub-arachnoid haemorrhage associated with traumatic head injury.

It has also been discovered that compounds possessing orexin receptor antagonist activity, in particular orexin-1 receptor antagonist activity, are useful for blocking the emetic response. The compounds are therefore of use in the treatment of nausea and vomiting associated with cancer therapy. The compounds are also of potential use in the treatment of post-operative or motion sickness.

It has also been discovered that compounds possessing orexin receptor antagonist activity, in particular orexin-1 receptor antagonist activity, may inhibit pain via an action on the peripheral C-fibres and are therefore useful in the treatment of conditions associated with visceral pain, such as irritable bowel syndrome and also migraine, angina and urge type incontinence such as inappropriate urge type incontinence associated with cystitis.

The present invention provides the use of an orexin receptor antagonist in the manufacture of a medicament for the treatment and/or prophylaxis of disorders associated with neuronal degeneration resulting from ischaemic events, the treatment and/or prophylaxis of nausea and vomiting, or the treatment and/or prophylaxis of irritable bowel syndrome or other conditions associated with visceral pain.

The present invention also provides a method for the treatment and/or prophylaxis of disorders associated with neuronal degeneration resulting from ischaemic events, the treatment and/or prophylaxis of nausea and vomiting, or the treatment and/or prophylaxis of irritable bowel syndrome or other conditions associated with visceral pain in mammals which comprises administering to a host in need thereof an effective amount of an orexin receptor antagonist or a pharmaceutically acceptable salt thereof.

When used in therapy, the orexin receptor antagonists are usually formulated in a standard pharmaceutical composition. Such compositions can be prepared using standard procedures.

The orexin receptor antagonist is preferably an orexin-1 receptor antagonist.

Orexin receptor antagonists may be administered by any convenient method, for example by oral, parenteral, buccal, sublingual, nasal, rectal or transdermal administration and the pharmaceutical compositions adapted accordingly.

Orexin receptor antagonists which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard A carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon or hydrofluorocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the orexin receptor antagonist used in the treatment or prophylaxis of the abovementioned disorders or diseases will vary in the usual way with the particular disorder or disease being treated, the weight of the subject and other similar factors. However as a general rule suitable unit doses may be 0.05 to 1000 mg, more suitably 0.05 to 500 mg; such unit doses may be administered more than once a day for example two or three times a day, so that the total daily dosage is in the range of about 0.01 to 100 mg/kg; and such therapy may extend for a number of weeks or months.

All U.S. patents cited in this specification are herein incorporated by reference as if each individual patent was specifically and individually indicated to be incorporated by reference herein as though fully set forth.

EXPERIMENTAL METHODS

Human orexin-A, referred to above, has the amino acid sequence:

```
pyroGlu Pro Leu Pro Asp Cys Arg Gln Lys Thr
   1            5                    10
Cys Ser Cys Arg Leu Tyr Glu Leu Leu His Gly Ala
       15                        20
Gly Asn His Ala Ala Gly Ile Leu Thr
       25              30
```

Orexin-A can be employed in a process for screening for compounds (antagonists) which inhibit the ligand's activation of the orexin-1 receptor.

In general, such screening procedures involve providing appropriate cells which express the orexin-1 receptor on the surface thereof. Such cells include cells from mammals, yeast, Drosophila or E. coli. In particular, a polynucleotide encoding the orexin-1 receptor is employed to transfect cells to thereby express the receptor. The expressed receptor is then contacted with a test compound and an orexin-1 receptor ligand to observe inhibition of a functional response.

One such screening procedure involves the use of melanophores which are transfected to express the orexin-1 receptor. Such a screening technique is described in WO 92/01810.

Another such screening technique involves introducing RNA encoding the orexin-1 receptor into Xenopus oocytes to transiently express the receptor. The receptor oocytes may then be contacted with a receptor ligand and a compound to be screened, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on the surface thereof. Such a method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand can be labelled, e.g. by radioactivity. The amount of labelled ligand bound to the receptors is measured, e.g. by measuring radioactivity of the receptors. If the compound binds to the receptor as determined by a reduction of labelled ligand which binds to the receptors, the binding of labelled ligand to the receptor is inhibited.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor. The ligand used in the screening method described below to determine orexin-1 receptor antagonist activity is orexin-A which has the amino acid sequence shown above.

Determination of Orexin-1 Receptor Antagonist Activity

The orexin-1 receptor antagonist activity of the compounds of formula (1) was determined in accordance with the following experimental method.

HEK293 cells expressing the human orexin-1 receptor were grown in cell medium (MEM medium with Earl's salts) containing 2 mM L-Glutamine, 0.4 mg/mL G418 Sulfate from GIBCO BRL and 10% heat inactivated fetal calf serum from Gibco BRL. The cells were seeded at 20,000 cells/100 µl/well into 96-well black clear bottom sterile plates from Costar which had been pre-coated with 10 µg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the 40 concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 µl of cell medium containing probenecid (Sigma) and Fluo3AM (Texas Fluorescence Laboratories) was added (Quadra, Tomtec) to each well to give final concentrations of 2.5 mM and 4 µM, respectively. The 96-well plates were incubated for 90 min at 37° C. in 5% $CO_2$. The loading solution containing dye was then aspirated and cells were washed with 4×150 $\mu$l Tyrode's buffer containing probenecid and 0.1% gelatin (Denley Cell Wash). The volume of buffer left in each well was 125 $\mu$l. Antagonist or buffer (25 $\mu$l) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, 1995, *TiPS*, 16, 413–417) to generate a concentration effect value. Antagonist Kb values were calculated using the equation:

$$K_b = IC_{50}/(1+([3/EC_{50}])$$

where $EC_{50}$ was the potency of human orexin-A determined in the assay (in nM terms) and $IC_{50}$ is expressed in molar terms.

Pharmacological Models

Stroke and/or Head Injury

The following method may be used to demonstrate the neuroprotectant efficacy of orexin receptor antagonists in a model of stroke and/or head injury.

Male rats are anaesthetised and focal ischaemia induced via permanent middle cerebral artery (MCA) occlusion by a method as described by Longa et al (1989) *Stroke*, 20, 84–91. In a model of head injury the iscaemic effects of traumatic head injury may also be simulated by causing trauma to the head. Twenty-four hours after MCA occlusion, rats are perfusion fixed with neutral buffered formalin (NBF) containing 5% sucrose. The brains are then serially sectioned (1.5 mm intervals) through the cerebrum from the anterior poles to the cerebellum and the sections (50 um) stained with Cresyl Fast Violet. The sections are examined and the areas of ischaenic damage delineated at 8 preselected coronal levels from anterior+3.0 mm to posterior–7.5 mm relative to bregma. Volumes are then corrected for hemispheric swelling. The test compound or vehicle is administered intravenously one hour post-MCA occlusion.

Inhibition of Chemotherapy Induced Nausea and Vomiting

Adult male ferrets (initial body weight 1.3–1.8kg) were individually housed, fed once daily (200 g Chum Puppy Food plus 50 g Lab Diet A) and were supplied with water ad libitum. Additionally, each animal was given ¼ pint of milk daily during an acclimatization period.

To facilitate intravenous administration of drugs, a chronic indwelling catheter was surgically implanted into the jugular vein using a modification of the technique described by Florczyk and Schurig, 1981 (*Pharmacol. Biochem. Behav.*, 14, 255–257). Prior to surgery each animal was sedated with ketamine hydrochloride (40 mg/animal intramuscularly) and anaesthetised with a halothane-$N_2O$—$O_2$ mixture. A four day recovery period was allowed before commencement of an experiment.

For each group of animals, a preliminary study was carried out to establish an intravenous dose level of cytotoxic agent(s) which would give a consistent and reproducible emetic response. The appropriate dose of example was administered intravenously twice to each animal; 30 minutes before and 30–45 minutes after dosing with cytotoxic agent (s). Running controls received vehicle and cytotoxic agent (s) only.

A single emetic response commenced when an animal assumed a characteristic posture with retching and was concluded when either vomitus was expelled or was present in the mouth as evidenced by a chewing movement. The total number of emetic responses was determined during the four hour period following administration of cytotoxic agent (s) and the number of animals completely protected from emesis determined for each treatment.

Urinary Bladder Incontinence

Micturition reflexes are measured in animals in response to intraluminal bladder distension. There are several methods by which the sensitivity to normal levels of bladder distension are increased, thereby inducing bladder hyperreactivity and hence, providing a means by which the beneficial effect of orexin-1 receptor antagonists can be measured. Usually, these involve the application of a particular pathology to a rat or other species. In one example, the frequency of bladder voiding reflexes are increased in anaesthetized rats by chemical irritation of the bladder, using agents such as acetic acid or capsaicin (e.g. Yu and de Groat, *Brain Research*, 1998, 807, 11–18); voiding reflexes are measured by recording intravesical pressure after catheterization of the bladder. Inhibitors of orexin-1 receptor-mediated function prevent this increase in bladder sensitivity.

Visceral Pain

The potential anti-migraine utility of orexin recptor antagonists may be evaluated in a range of models thought to represent the development of migraine (Chen et al., 1999 *Bioorg. Med. Chem. Lett.*, 1999, 9: 285–290; Raval et al., *Br. J. Pharmacol.*, 1999, 126: 485–493; Read et al., *Cephalalgia*, 1997, 17: 826–832) or by anti-hyperalgesic properties (Bingham et al., 1999 *Cephalalgia* in press IHS meeting abstract).

Irritable Bowel Syndrome as Associated with Intestinal Pain

Male Wistar rats (180–450 g), housed individually and fasted overnight, were used. Under halothane (4–5%) anaesthesia, a 6–7 cm long latex balloon was inserted intra-anally to a position approximately 1 cm beyond the ano-rectal verge. The cannula from the balloon was taped to the tail to prevent its expulsion and was connected to a pressure transducer linked to a pen recorder via a 3-way tap and a peristaltic pump. Throughout the procedure the singly-housed animals were allowed unrestricted movement. After full recovery from anaesthesia, as determined by recovery of righting reflex and stable gait, a ramp inflation of the colo-rectal balloon was performed until the visceromotor threshold was observed as contraction of the abdominal muscles. At this point the stimulus was immediately removed by opening the 3-way tap to air. The threshold distension pressure was noted from the pen recorder. This inflation procedure was repeated at 5 min intervals for up to 75 min, during which time constant responses are evoked with thresholds of between 10–40 mmHg. Orexin receptor antagonists, or saline were dosed sc after 3 stable responses to colo-rectal distension were achieved and within 45 min of dosing with any substance which might evoke intestinal allodynia. Further distensions were performed at 5 min intervals over 30 min. If, at any time, the distension pressure reached 100 mmHg without observation of the visceromotor reflex then that inflation procedure was terminated and the stimulus removed. Changes in the distension pressure required to evoke the visceromotor reflex were compared with the mean of the three pre-dose stable recordings which was taken to be 100%.

What is claimed is:

1. A method of treatment or prophylaxis of a disorder associated with neuronal degeneration resulting from an ischaemic event, nausea and vomiting, irritable bowel syndrome or a condition associated with visceral pain comprising adminstering to a mammal in need thereof an effective amount of an orexin receptor antagonist or a pharmaceutically acceptable salt thereof.

2. A method according to claim 1 for the treatment or prophylaxis of said disorder associated with neuronal degeneration resulting from an ischaemic event.

3. A method according to claim 2 wherein said ischaemic event is cerebral ischaemia after cardiac arrest, stroke or multi-infarct dementia, a cerebral ischaemic event resulting from surgery or during childbirth, or a disorder resulting from traumatic head injury and subsequent haemorrhaging.

4. A method according to claim 2 for the treatment or prophylaxis of stroke or sub-arachnoid haemorrhage.

5. A method according to claim 1 for the treatment or prophylaxis of nausea and vomiting.

6. A method according to claim 5 the treatment or prophylaxis of nausea and vomiting associated with cancer therapy or post-operative or motion sickness.

7. A method according to claim 1 for the treatment or prophylaxis of irritable bowel syndrome.

8. A method according to claim 1 for the treatment of said condition associated with visceral pain.

9. A method according to claim 8 wherein the condition associated with visceral pain is migraine, angina or urge type incontinence.

10. A method according to claim 1 wherein the orexin receptor antagonist is an orexin-1 receptor antagonist.

* * * * *

SEQUENCE LISTING

```
<160> NUMBER OF SEQ ID NOS: 1

<210> SEQ ID NO 1
<211> LENGTH: 33
<212> TYPE: PRT
<213> ORGANISM: human

<400> SEQUENCE: 1

Glu Pro Leu Pro Asp Cys Cys Arg Gln Lys Thr Cys Ser Cys Arg Leu
 1               5                  10                  15

Tyr Glu Leu Leu His Gly Ala Gly Asn His Ala Ala Gly Ile Leu Thr
            20                  25                  30

Leu
```